United States Patent
Smith

(10) Patent No.: US 9,044,415 B2
(45) Date of Patent: Jun. 2, 2015

(54) METHOD FOR MAKING SYNTHETIC SEBUM FOR HAIR TRANSFORMATION

(71) Applicant: Suddian S. Smith, Kissimmee, FL (US)

(72) Inventor: Suddian S. Smith, Kissimmee, FL (US)

(*) Notice: Subject to any disclaimer, the term of this patent is extended or adjusted under 35 U.S.C. 154(b) by 0 days.

(21) Appl. No.: 14/078,791

(22) Filed: Nov. 13, 2013

(65) Prior Publication Data

US 2014/0060567 A1 Mar. 6, 2014

Related U.S. Application Data

(63) Continuation-in-part of application No. 12/928,429, filed on Dec. 13, 2010, now abandoned.

(51) Int. Cl.
| | |
|---|---|
| *A61Q 5/06* | (2006.01) |
| *A61Q 5/12* | (2006.01) |
| *A61K 8/92* | (2006.01) |
| *A61K 8/891* | (2006.01) |
| *A61K 8/73* | (2006.01) |
| *A45D 7/04* | (2006.01) |

(52) U.S. Cl.
CPC . *A61K 8/922* (2013.01); *A61Q 5/12* (2013.01); *A61K 8/891* (2013.01); *A61K 8/732* (2013.01); *A61K 8/92* (2013.01); *A61K 8/925* (2013.01); *A45D 7/04* (2013.01); *A61Q 5/06* (2013.01); *A61K 8/927* (2013.01)

(58) Field of Classification Search
None
See application file for complete search history.

(56) References Cited

U.S. PATENT DOCUMENTS

2005/0175646 A1 * 8/2005 Catroux et al. ............... 424/401

* cited by examiner

*Primary Examiner* — Jyothsna Venkat
(74) *Attorney, Agent, or Firm* — Terry M. Sanks, Esq.; Cian G. O'Brien, Esq.; Beusse Wolter Sanks & Maire, P.A.

(57) ABSTRACT

A method is presented for forming a synthetic sebum for transforming hair. The method includes mixing water with a thickening agent at a first temperature to form a first mixture and mixing water with a sequestering agent, a first preservative and a second preservative to form a second mixture. The method further includes mixing the first and second mixture to form a third mixture. The method further includes a thickening agent with the third mixture to form a fourth mixture and mixing an antifoam agent with the fourth mixture to form a fifth mixture. The method further includes one or more of: mixing one or more waxes with the fifth mixture; mixing an emulsifying wax with the fifth mixture and/or mixing one or more oils with the fifth mixture.

13 Claims, 4 Drawing Sheets

METHOD FOR MAKING SYNTHETIC SEBUM FOR HAIR TRANSFORMATION

CROSS-REFERENCE TO RELATED APPLICATIONS

This application is a Continuation-in-Part to U.S. patent application Ser. No. 12/928,429 filed on Dec. 13, 2010, and is incorporated by reference herein in its entirety.

FIELD OF THE INVENTION

The invention relates to hair treatment products and, more specifically, to a method for making a synthetic sebum to be used to transform hair from a first hair type to a second hair type.

BACKGROUND OF THE INVENTION

In today's glamour-conscious society, a person's appearance can greatly impact such factors as social status and economic success. Looking one's best is often a top priority for an individual. Many beautifying treatments have been developed for the treatment of hair, and continue to be developed. These include hair color or bleaching treatments for people who want a different color hair or hair relaxation treatments for people with curly or kinky hair, each of which alters the chemical structure of the hair. In general, the more radical the change in hair appearance, the greater will be the chemical alteration of, and potential damage to, the hair. Those with kinky hair usually have hair that is coarse and unmanageable. To solve the problem they resort to using chemicals to make hair look more like other hair textures, such as curly, wavy, or straight hair.

Most hair textures have a natural moisture called sebum that is useful in protecting the hair. Chemical hair treatments can strip away this natural moisture. For some hair types, such as kinky hair, the natural sebum is not produced at the same levels as other hair types. Thus, when people with kinky hair treat their hair with chemicals, they strip away the small amount of natural sebum that resides on their hair, resulting in the hair becoming dry, dull, frayed, broken, splitted, and damaged over time. Although untreated kinky hair may exhibit some degree of being dry, dull, frayed and broken, treating the hair with chemicals worsens the severity of these characteristics in the hair.

In contrast with kinky hair, other hair types such as curly hair produce a higher amount of natural sebum, and thus the properties of curly hair are sought out by those individuals with kinky hair. Hence, these individuals employ the use of chemicals to treat their hair, without realizing that the chemicals will break down the already small amount of natural sebum in their hair, resulting in the hair becoming even more dry, dull and damaged. Indeed, the damage to the hair as a result of these chemical treatments is permanent, and thus the individual needs to re-grow their hair in its natural state to achieve undamaged hair.

A natural dilemma is encountered by people with kinky hair and who are required by their profession to have well groomed hair. Kinky hair in its natural state is often not preferable in the professional work environment, and thus a permanent chemical relaxer or permanent waving product is often the only solution for taming unruly kinky hair. However, this results in merely a short term solution and long-term irreparable damage to the hair, as discussed above. Indeed, individuals with kinky hair have fewer strands of hair than individuals with other hair types, which is why chemical treatment of the hair results in side effects of the hair looking thin, limp and with no volume or bounce. Another side effect of chemical treatment on hair is loss of the outer cuticle layer, as well as change in the porosity of the hair, which permits moisture to pass out of the hair and water and other chemicals to be absorbed into the hair. Low sebum, thin weak strands, and high porosity are all natural characteristics that describe kinky hair in it natural state.

Hair creams and gels are water based and are absorbed by kinky hair and thus will not create change after being absorbed. If change is to take place, the styling product must sit outside the hair cuticle, and coat the shaft of the hair. This coating would serve to protect the hair cuticle. Since kinky hair has low sebum, it lacks the protection to prevent water and harmful chemicals from being absorbed into the hair quickly and to prevent moisture on the hair to being quickly lost. If sebum were present on the kinky hair, it would naturally protect the hair against absorption of water and harmful agents as well as prevent the loss of moisture on the hair. Other hair textures, such as curly hair, wavy hair and straight hair, have lower porosity, such that applied creams and gels sit outside the hair cuticle and coat the outer hair strands so that moisture is retained and not lost. The sebum in the hair types prevents the loss of moisture and prevents the absorption of water and harmful substances through the hair cuticle.

Conventional methods have been used to vary the style of kinky hair to curly hair, but these methods are temporary. For example, heat styling such as blow-drying, flat ironing, hot combing, and hot curling can allow the hair to become straight temporarily without the use of chemicals. However, heat styling performed on kinky hair, to convert kinky hair to curly hair will only last a couple days and much shorter if the hair is exposed to humidity, rain or a hot shower. Additionally, the heat styling method causes damage over time, since the heat causes split ends and other damage to the hair shaft, resulting in the hair breaking and looking dry. Furthermore, the heat styling appliances can be very expensive and multiple appliances may be needed to do the job.

In order for the hair to be moisturized, free from breakage, strong, protected, smooth, shiny, sleek, and grow it needs a sufficient amount of sebum. Natural sebum is made by the body and secreted through the sebaceous glands beneath our scalp, to provide a natural protection for the hair. Sebum glides from the root down the hair shaft to the tip. The sebum slides down to the hair tip relatively quickly with straight hair, and at a slower rate with wavy and curly hair, since the sebum has to go through several curves to get from the root to the tip. However, little to no sebum reaches the tip of kinky hair, since the sebum has a difficult time traveling on the hair shaft due to its irregular shape. Lack of sebum contributes to the kinky hair being rough, coarse, and unmanageable.

BRIEF DESCRIPTION OF THE INVENTION

In one embodiment of the present invention, a method is presented for forming a synthetic sebum for transforming hair from a first hair type to a second hair type. The method includes mixing water with a thickening agent at a first temperature to form a first mixture. The method also includes mixing water with a sequestering agent, a first preservative and a second preservative at the first temperature to form a second mixture. The method also includes mixing the first mixture and the second mixture to form a third mixture. The method also includes mixing a thickening agent with the third mixture to form a fourth mixture and mixing an antifoam agent with the fourth mixture to form a fifth mixture. The method also includes one or more of the following steps:

mixing at least one wax with the fifth mixture; mixing an emulsifying wax with the fifth mixture; and mixing at least one oil with the fifth mixture.

In another embodiment of the present invention, a method is presented for forming a synthetic sebum for transforming hair from a first hair type to a second hair type. The method includes mixing water with a thickening agent at a first temperature to form a first mixture. The method also includes one or more of the following steps: mixing at least one wax with the first mixture; mixing an emulsifying wax with the first mixture; and mixing at least one oil with the first mixture.

In another embodiment of the present invention, a method is presented for forming a hair transformation agent for transforming hair. The method includes mixing liquid starch with beeswax, emulsifying wax and at least one oil into a mixture. The method also includes heating the mixture and mixing at least one oil, alkyl benzoate and mica and titanium dioxide into the heated mixture until the mixture is cool.

In another embodiment of the present invention, a method is presented for using a synthetic sebum for transforming hair from a first hair type to a second hair type. The method includes washing the hair, towel drying the hair and spraying the hair with a mixture of water, conditioner and oil. The method further includes smoothing the mixture into the hair and removing excess liquid from the hair. The method further includes separating the hair into sections and applying synthetic sebum to each section of the hair using an application technique. The method further includes waiting a period of time for the hair to dry naturally.

DETAILED DESCRIPTION OF THE INVENTION

Figure 1:
FIG. 1 illustrates a plan view of a plurality of different hair types.
Figure 1:
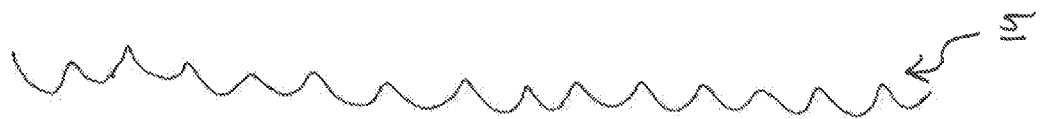
Figure 1:
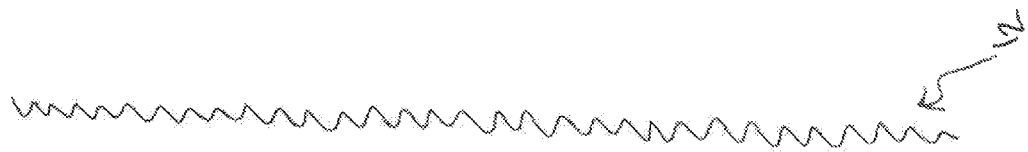
Figure 1:

The inventor of the present invention recognized that individuals with kinky hair, in an effort to improve their hair, routinely use chemical treatments for short-term treatment of their hair, resulting in permanent long-term damage to their hair. The inventor of the present invention also recognized that the presence of sebum in the hair is synonymous with texture, and thus more sebum in the hair will result in smoother texture, straighter hair, more manageable hair, and easier to comb, shiny, healthy looking and stronger hair that is less susceptible to breakage. Additionally, the inventor of the present invention recognized that kinky hair has little to no sebum along the hair shaft from the root to the tip and that even if sebum were accumulated on the scalp, the sebum would not easily travel down the hair shaft to the tip, due to the irregular hair shape. Based on these observations, the inventor of the present invention created a formula for synthetic sebum that simulates natural sebum. The inventor recognized that if a synthetic sebum could be developed and applied along the shaft of kinky hair, from the root to the tip, the hair characteristics would improve without any long-term damage.

Additionally, the inventor of the present invention recognized that creams that are routinely used to treat kinky hair includes ingredients such as petroleum and other oily moisturizing agents, resulting in greasy kinky hair which is just as undesirable as dry kinky hair. The inventor of the present invention also recognized that a natural sebum product would achieve the desired improvement in characteristics in kinky hair, such as improved texture, straighter, more manageable, as well as shinier hair, without the permanent long-term damage experienced with chemical treatment. The inventor of the present invention recognized that creating synthetic sebum and treating the hair with synthetic sebum transforms the kinky hair via a physical process, rather than a chemical process, as with conventional treatments.

The present invention discusses a method for making a synthetic sebum for hair that can be applied to hair and used to transform the hair from a first hair type to a second hair type, such as from a kinky hair type to a curly hair type, for example.

TABLE 1

| Phase | Ingredients | In mL |
|---|---|---|
| A | Water | 400-600 |
| A | Corn Starch | 40-80 |
| B | Water | 230-450 |
| B | Tetrasodium EDTA | 0.10-3.5 |
| B | Sodium Tetraborate Decahydrate (Borax) | 1-30 |
| B | Sodium Metabisulfite | 0.10-3.5 |
| C | Cyclocarboxypropyloleic Acid Potassium Salt 40% solution (DIACID H-240) | 50-200 |
| C | Dimethicone (antifoam agent) | 0.01-10 |

Table 1 above lists the ingredients that are used in the process of making the synthetic sebum, and further lists each phase in which the ingredients are mixed. In a first phase A, an amount within a range of 400-600 ml of water is mixed with an amount within a range of 40-80 ml of corn starch at a temperature within a range of between 60-70° C. (140-158° F.) until the starch has completely dissolved and a first mixture, a clear, viscous liquid, is obtained. The water and corn starch should be mixed continuously so that the mixture does not transform into a glue. In an exemplary embodiment, in the first phase A, 500 ml of water may be mixed with 60 ml of corn starch at a temperature of 65° C. (149° F.), for example. However, this example is merely exemplary and any amount of water and corn starch within the above ranges may be used and heated at any temperature within the above range. Additionally, although corn starch is disclosed above as being mixed with water, any thickening agent or stiffening agent may be mixed with water during the first phase A.

As further listed in Table 1, during a second phase B in the process of making the synthetic sebum, an amount within a range of 230-450 ml of water, an amount within a range of 0.10-3.5 ml of Tetrasodium EDTA, an amount within a range of 1-30 ml of Sodium Tetraborate Decahydrate (Borax), and an amount within a range of 0.10-3.5 of Sodium Metabisulfite are mixed at a temperature within a range of between 60-70° C. (140-158° F.) until each of the ingredients are dissolved in the water to form a second mixture. In an exemplary embodiment, in the second phase B of forming the first part, 332 ml of water may be mixed with 0.50 ml of Tetrasodium EDTA, 7.5 ml of Sodium Tetraborate Decahydrate and 0.10 ml of Sodium Metabisulfite at a temperature of 65° C. (149° F.), for example. However, this example is merely exemplary and any amount of the water, Tetrasodium EDTA, Sodium Tetraborate Decahydrate and Sodium Metabisulfite within the above ranges may be used, and heated at any temperature within the above temperature range. Additionally, any sequestering agent other than Tetrasodium EDTA, any preservative to maintain a stable pH other than Sodium Tetraborate Decahydrate and any preservative to inhibit microbe growth other than Sodium Metabisulfite may be mixed with the water during the second phase B.

As further listed in Table 1, during a third phase C in the process of making the synthetic sebum, the first mixture resulting from the first phase A is mixed with the second mixture resulting from the second phase B, to form a third mixture while slowing mixing the combined mixtures. Additionally, during the third phase C, after mixing the mixtures from the first and second phases, an amount within a range of 50-200 ml of Cyclocarboxypropyloleic Acid Potassium Salt 40% Solution is added to the third mixture and continuously mixed until a fourth mixture is obtained that is homogeneous. Additionally, during the third phase C, an amount within a range of 0.01-10 ml of Dimethicone is added to the fourth mixture and continuously mixed until a fifth mixture is obtained that is homogeneous. In an exemplary embodiment, in the third phase C, 100 ml of Cyclocarboxypropyloleic Acid Potassium Salt 40% Solution may be mixed along with 0.10 ml of Dimethicone. However, this example is merely exemplary and any amount of the Cyclocarboxypropyloleic Acid Potassium Salt 40% Solution and Dimethicone within the above ranges may be used. Additionally, any thickening agent or skin conditioning agent other than Cyclocarboxypropyloleic Acid Potassium Salt 40% Solution and any antifoam agent or film former other than Dimethicone may be mixed during the third phase C.

In an alternate embodiment, if a colorant or fragrance is desired in the synthetic sebum, an amount such as 2 mL or less, for example, of colorant and/or fragrance may be added to the fourth mixture during the third phase C, after adding the Cyclocarboxypropyloleic Acid Potassium Salt 40% Solution. The amount of colorant and/or fragrance that is added during the third phase C may be subtracted from the amount of the water that is used during the second phase B. As discussed above, the addition of colorant and/or fragrance is merely optional and the synthetic sebum need not include colorant and/or fragrance in order to transform hair from a first type to a second type, such as from a kinky hair type to a curly hair type.

Table 2 below lists additional ingredients that are used to form the synthetic sebum, and further lists each phase in which the ingredients are mixed.

TABLE 2

| Phase | Ingredients | In ML |
|---|---|---|
| D | Water | 0.5-100 |
| D | Gum Arabic - Powder | 0.5-100 |
| E | Phase A-C Mixture | 20-400 |
| F | Wax of choice - Beeswax | 0.01-200 |
| F | Wax of Choice - Soy Wax | 0.01-200 |
| F | Wax of choice - Jojoba Ester/Jojoba oil (wax) | 0.01-200 |
| F | Wax of choice - Emulsifying wax (Other unmentioned waxes can also be used in phase F) | 0.01-200 |
| G | Emulsifier - Emulsifying wax | 0.01-90 |
| H | Oils e.g. carrier oils or essential oils (grape seed, safflower, jojoba, argan, castor, fractionated coconut) oil or any other suitable carrier oil OR Petroleum Jelly | 0.01-200 |
| I | Fractionated Coconut Oil | 0.01-200 |
| I | Castor Oil | 0.01-150 |
| J | Crodamol AB-LQ (MH) | 0.01-50 |
| K | UCON 50-HB-3520 | 0.01-25 |
| K | Any Pack Hair Conditioner heavy, thick | 0.01-150 |

In a fourth phase D, an amount within a range of 0.5-100 ml of water is mixed with an amount within a range of 0.5-100 ml of gum Arabic powder for a time within a range of 1-3 minutes, after which the mixture is allowed to stand for 10-15 minutes. In an exemplary embodiment, an equal amount of water and gum Arabic powder are mixed during the fourth phase D. However, equal amounts of water and gum Arabic powder need not be mixed during the fourth phase D and, for example, half as much gum Arabic powder may be used as water during the fourth phase D. After the mixture is allowed to stand for 10-15 minutes, the mixture is continuously stirred until a smooth golden brown liquid is formed. In an exemplary embodiment, in the fourth phase D of forming the synthetic sebum, 5 ml of water may be mixed with 5 ml of gum Arabic powder for a time of 2 minutes, before the mixture is allowed to stand for 10-15 minutes, for example. However, this example is merely exemplary and any amount of water and gum Arabic powder within the above ranges may be used for any time within the above range. Additionally, although gum Arabic powder is disclosed above as being mixed with water, any thickening agent or stabilizer may be mixed with water during the fourth phase D of forming the synthetic sebum.

In a fifth phase E, an amount within a range of 20-400 ml of the fifth mixture obtained from the A-C phases is collected at room temperature. In a sixth phase F, the amount of the fifth mixture from the fifth phase E is mixed with an amount within a range of 0.01-200 ml of beeswax to form a sixth mixture. In an exemplary embodiment, in the sixth phase F of forming the synthetic sebum, 120 ml of the fifth mixture may be mixed with 120 ml of beeswax. However, this example is merely exemplary and any amount of the fifth mixture and beeswax within the above ranges may be used. Additionally, although beeswax is disclosed above as being mixed with the fifth mixture, one or more waxes including beeswax, soy wax, jojoba ester, jojoba wax, emulsifying wax, natural or synthetic wax, plant or animal wax, petroleum derived wax, polyethylene and related derivatives and/or any wax capable of increasing viscosity may be used, where the total volume of all of the waxes used is within the above range for the beeswax.

In a seventh phase G, an amount within a range of 0.01-90 ml of emulsifying wax is mixed with the sixth mixture from the sixth phase F to act as an emulsifier between the waxes and liquids from the phases D-F to form a seventh mixture. In an exemplary embodiment, in the seventh phase G of forming the synthetic sebum, 7.5 ml of the emulsifying wax may be mixed with the sixth mixture, for example. However, this example is merely exemplary and any amount of the emulsifying wax within the above range may be used. Additionally, although emulsifying wax is disclosed above as being mixed with the sixth mixture, any emulsifier may be mixed with the sixth mixture during the seventh phase G of forming the synthetic sebum.

In an eighth phase H, an amount within a range of 0.01-200 ml of one or more oils is mixed with the seventh mixture from the seventh phase G to form an eighth mixture. In an exemplary embodiment, in the eighth phase H of forming the second part, 30 ml of oils may be mixed with the seventh mixture from seventh phase G, for example. However, this example is merely exemplary and any amount of oils within the above range may be used. Additionally, any oil including carrier oils and/or essential oils, such as grape seed oil, safflower oil, lubricant, plant or animal oil, any oil derived from organisms, mineral oil, petroleum oil, crude oil or waxes with oil-characteristics such as jojoba oil, and argan oil may be mixed with the seventh mixture from the seventh phase G, provided that the combined amount of the oils is within the above range.

In an exemplary embodiment, although the above description discusses eight phases A-H in the formation of the synthetic sebum, the process need not include all of these eight phases, nor the additional phases beyond the eighth phase discussed in further detail below. In a preferred embodiment, the synthetic sebum may be formed using phases A-C, E and one or more of the phases F-H. Although the above description discusses that the phases F-H are performed in sequence, this is not required and the ingredients from each phase F-H may be added to the fifth mixture from the fifth phase E. In one embodiment, the synthetic sebum may be formed using phases A-C, E and F, for example. In one embodiment, the synthetic sebum may be formed using phases A-C, E and F-G, for example. In one embodiment, the synthetic sebum may be formed using phases A-C, E, F and H, for example. In one embodiment, the synthetic sebum may be formed using phases A-C, E and F-H, for example. In another embodiment, the synthetic sebum may be formed using phases A-C, E and G, for example. In one embodiment, the synthetic sebum may be formed using phases A-C, E, G and H, for example. In another embodiment, the synthetic sebum may be formed using phases A-C, E and for example.

In another preferred embodiment, the synthetic sebum may be formed using phase A and one or more of the phases F-H. Indeed, although the above description discusses that the phases F-H are performed in sequence, and that the sixth phase F is performed on the fifth mixture from the fifth phase E, this is not required, and each of the ingredients from the one or more phases F-H that are employed may be added to the first mixture from the first phase A, to obtain an exemplary embodiment of the synthetic sebum. In one embodiment, the synthetic sebum may be formed using phases A and F, for example. In one embodiment, the synthetic sebum may be formed using phases A and F-G, for example. In one embodiment, the synthetic sebum may be formed using phases A, F and H, for example. In one embodiment, the synthetic sebum may be formed using phases A and F-H, for example. In another embodiment, the synthetic sebum may be formed using phases A and G, for example. In one embodiment, the synthetic sebum may be formed using phases A, G and H, for example. In another embodiment, the synthetic sebum may be formed using phases A and H, for example. Although the phases beyond the eighth phase H are not needed to form the synthetic sebum, these phases are discussed below, and may be optionally employed, in order to obtain other embodiments of the synthetic sebum with varying characteristics.

In a ninth phase I, an amount within a range of 0.01-200 ml of fractionated coconut oil is mixed with the eighth mixture from the eighth phase H to form a ninth mixture. In an exemplary embodiment, in the ninth phase I of forming the synthetic sebum, 10 ml of fractionated coconut oil is mixed with the eighth mixture from phase H, for example. However, this example is merely exemplary and any amount of fractionated coconut oil within the above range may be used. Additionally, during the ninth phase I, an amount within a range of 0.01-150 ml of castor oil is mixed with the eighth mixture from phase H. In an exemplary embodiment, in the ninth phase I of forming the synthetic sebum, 15 ml of castor oil is mixed with the eighth mixture from phase H, for example. However, this example is merely exemplary and any amount of castor oil within the above range may be used.

In a tenth phase J, an amount within a range of 0.01-50 ml of Crodamol AB-LQ is mixed with the ninth mixture from phase I to form a tenth mixture. In an exemplary embodiment, in the tenth phase J of forming the second part, 20 ml of Crodamol AB-LQ is mixed with the ninth mixture from phase I, for example. However, this example is merely exemplary and any amount of Crodamol AB-LQ within the above range may be used. Additionally, although Crodamol AB-LQ is disclosed above as being mixed with the solution from phase I, any emollient ester may be mixed with the ninth mixture from phase I during the tenth phase J of forming the synthetic sebum. The tenth mixture is then mixed vigorously until it has a thick, creamy consistency and is at room temperature. In an alternate embodiment, an electronic mixing device may be used to mix the mixture at the tenth phase J, to achieve this thick, creamy consistency.

In an eleventh phase K, an amount within a range of 0.01-25 ml of UCON 50-HB-3520 is mixed with the tenth mixture from phase J to form an eleventh mixture. In an exemplary embodiment, in the eleventh phase K of forming the second part, 2.5 ml of UCON 50-HB-3520 is mixed with the tenth mixture from phase J, for example. However, this example is merely exemplary and any amount of UCON 50-HB-3520 within the above range may be used. Additionally, although UCON 50-HB-3520 is disclosed above as being mixed with the tenth mixture from phase J, any UCON fluid or any lubricant may be mixed with the tenth mixture from phase J during the eleventh phase K of forming the synthetic sebum. Additionally, during the eleventh phase K, an amount within a range of 0.01-150 ml of hair conditioner is mixed with the tenth mixture from phase J. In an exemplary embodiment, in the eleventh phase K of forming the synthetic sebum, 16 ml of hair conditioner is mixed with the tenth mixture from phase J, for example. Additionally, although hair conditioner is disclosed as being mixed with the tenth mixture from phase J, any moisturizer, anti-sticking agent, smoothing agent, or lubricant may be mixed with the tenth mixture from phase J during the eleventh phase K of forming the synthetic sebum. However, this example is merely exemplary and any amount of hair conditioner within the above range or outside the above range may be used.

In a twelfth phase, an amount within a range of 2-3 ml of the fourth mixture from the fourth phase D is mixed with the mixture from the eleventh phase K, to obtain the synthetic sebum. In an exemplary embodiment, in the twelfth phase, 2.5 ml of the fourth mixture from the fourth phase D is mixed with the mixture from the eleventh phase K, to obtain the synthetic sebum, for example. However, this example is merely exemplary and any amount of the mixture from the fourth phase D within the above range may be used.

In an optional thirteenth phase, a color and/or a fragrance additive may be added to the synthetic sebum obtained during the twelfth phase, after which the mixture is mixed vigorously. After the color and/or fragrance additive have been added to the synthetic sebum and vigorously mixed, the mixture is allowed, to stand for an extended period of time, such as 24 hours, for example. However, as discussed above, the thirteenth phase discussed above is optional, the color and/or fragrance additives need not be added to the synthetic sebum and the mixture need not stand for any minimum period of time, provided that the mixture is permitted to stand for a necessary amount of time for the mixture to settle and cool.

As discussed above, the process for forming the synthetic sebum need not involve all of the above-discussed thirteen phases A-K. For example, the process for forming the synthetic sebum may only involve the first phase A and one or more of the phases F-H. In another example, the process for forming the synthetic sebum may only involve phases A-C, E and one or more of the phases F-H. In other examples, one or more of phases I-K may be employed, based on the desired characteristics of the synthetic sebum. In an exemplary embodiment, any of the phases may be used to form the synthetic sebum, provided that the formed synthetic sebum has the desired characteristics of being capable of physical transformation of a first hair type to a second hair type, such as physical transformation of a kinky hair type to a curly hair type.

FIG. 1 illustrates various hair types, such as a kinky hair type 10, a kinky-curly hair type 12, a curly hair type 14, and a wavy hair type 16. As previously discussed, the synthetic sebum formed based on the disclosed processes of the present invention are used to physically transform a first hair type to a second hair type, such as to physically transform the kinky hair type 10 to the kinky-curly hair type 12, for example. As illustrated in FIG. 1, the illustrated hair types are differentiated based on the increasing diameter of their curvature. For example, the kinky hair type 10 includes hair with the smallest diameter of curvature, whereas the kinky-curly hair type 12 includes hair with a larger diameter of curvature, as compared to the kinky hair type 10. The curly hair type 14 and wavy hair type 16 further include increasing diameter of curvature. The synthetic sebum formed based on the processes of the present invention permit one to physically transform a hair type from a first hair type of a lesser diameter of curvature to a second hair type with a greater diameter of curvature, such as from the kinky hair type 10 to the kinky-curly hair type 12, without incurring any permanent change or damage to the hair. Additionally, the synthetic sebum may be used to physically transform the kinky-curly hair type 12 to the curly hair type 14, or to physically transform the curly hair type 14 to the wavy hair type 16, for example.

Figure 2:
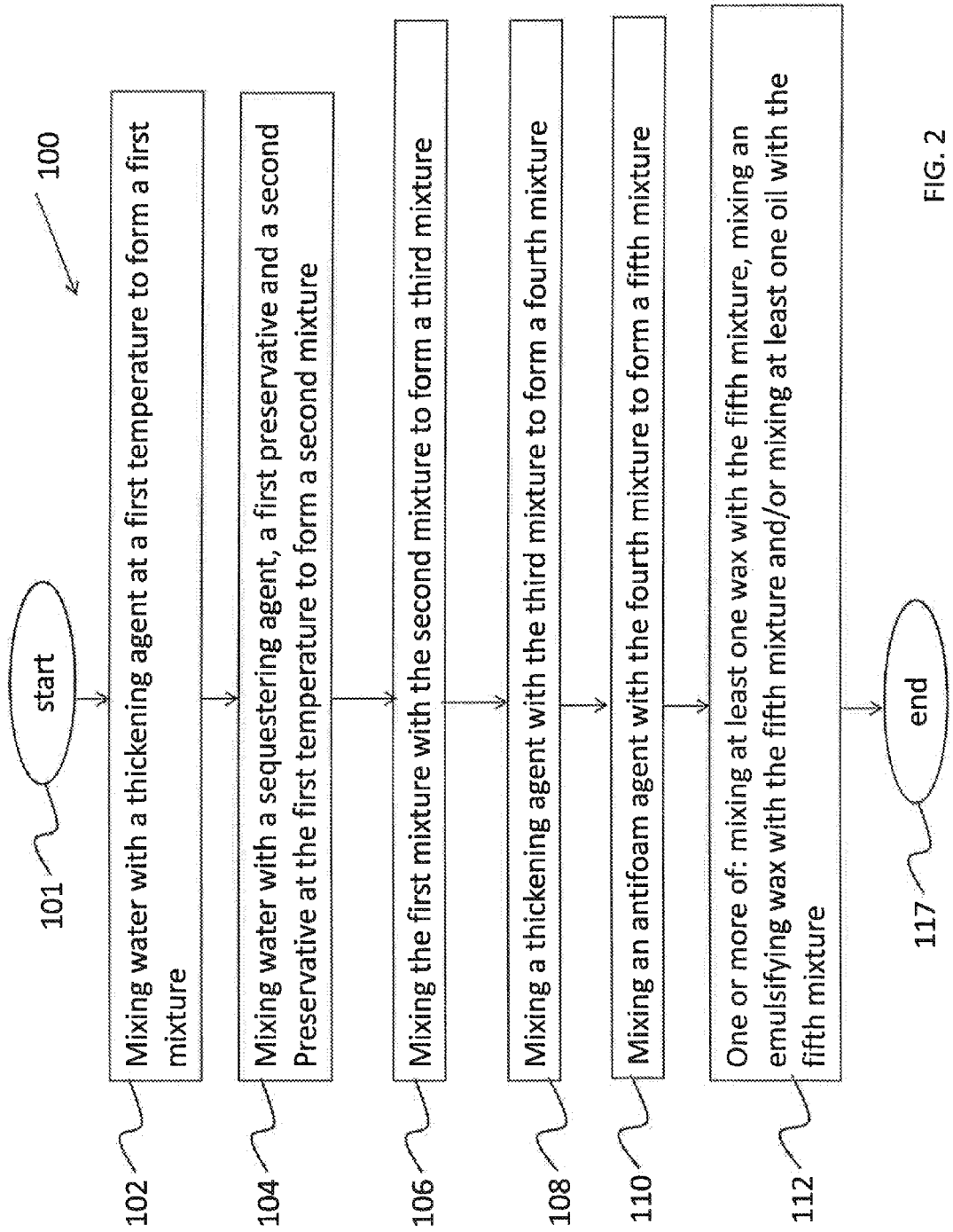
FIG. 2 illustrates a flow chart depicting a method for forming a synthetic sebum for transforming hair from a first hair type to a second hair type.

FIG. 2 illustrates a flow chart depicting a method 100 for forming a synthetic sebum for transforming hair from a first hair type to a second hair type. The method 100 starts at 101 by mixing 102 water with a thickening agent at a first temperature to form a first mixture. The method 100 further includes mixing 104 water with a sequestering agent, a first preservative and a second preservative at the first temperature to form a second mixture. The method 100 further includes mixing 106 the first mixture with the second mixture to form a third mixture. The method 100 further includes mixing 108 a thickening agent with the third mixture to form a fourth mixture. The method 100 further includes mixing 110 an antifoam agent with the fourth mixture to form a fifth mixture. The method 100 further includes one or more of: mixing 112 one or more waxes with the fifth mixture; mixing 114 an emulsifying wax with the fifth mixture; and mixing 116 one or more oils with the fifth mixture, before ending at 117. In another embodiment of the method, the method 100 may be performed without steps 104, 106, 108, 110, in which case the first mixture obtained after the mixing 102 step is used to perform one or more of the steps 112, 114, 116. Although the method 100 discusses several mixing steps, the method does not require that all of the above mixing steps be performed, provided that those mixing steps which are performed do achieve a synthetic sebum that is capable of physical transformation of a first hair type to a second hair type, without damaging the hair, as previously discussed. The range of amounts of each ingredient that is to be used in the above method is previously discussed and shown in Tables 1 and 2. However, the range of amounts of each ingredient is not limited to the above discussed ranges and may include any amount range, provided that the resulting mixture of ingredients achieve a synthetic sebum capable of physical transformation of the hair from a first hair type to a second hair type, without resulting in damage to the hair.

Figure 3:
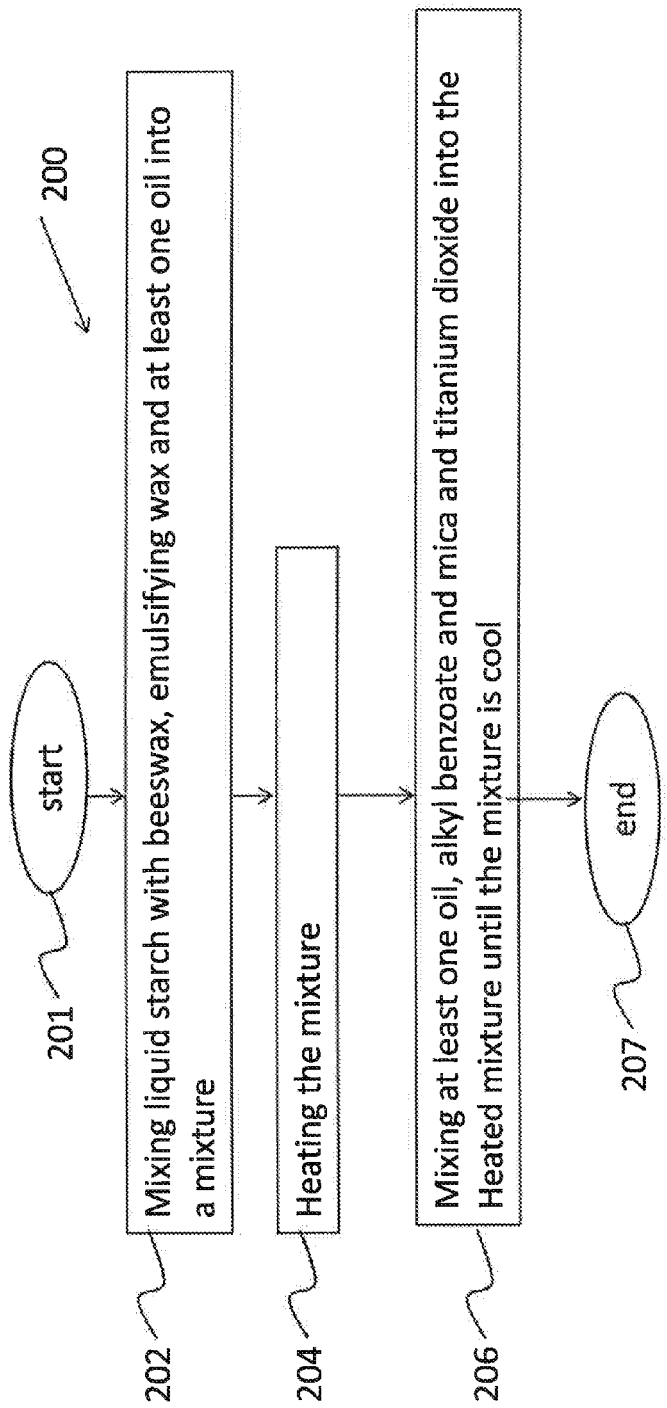
FIG. 3 illustrates a flow chart depicting a method for forming a hair transformation agent for transforming hair.

FIG. 3 illustrates a flowchart depicting a method 200 for forming a hair transformation agent, such as synthetic sebum, for transforming hair. The method 200 begins at 201 by mixing 202 liquid starch with beeswax, emulsifying wax and at least one oil into a mixture. The method 200 further includes heating 204 the mixture and mixing 206 at least one oil, alkyl benzoate and mica and titanium dioxide into the heated mixture until the mixture is cool, before ending at 207.

Figure 4:
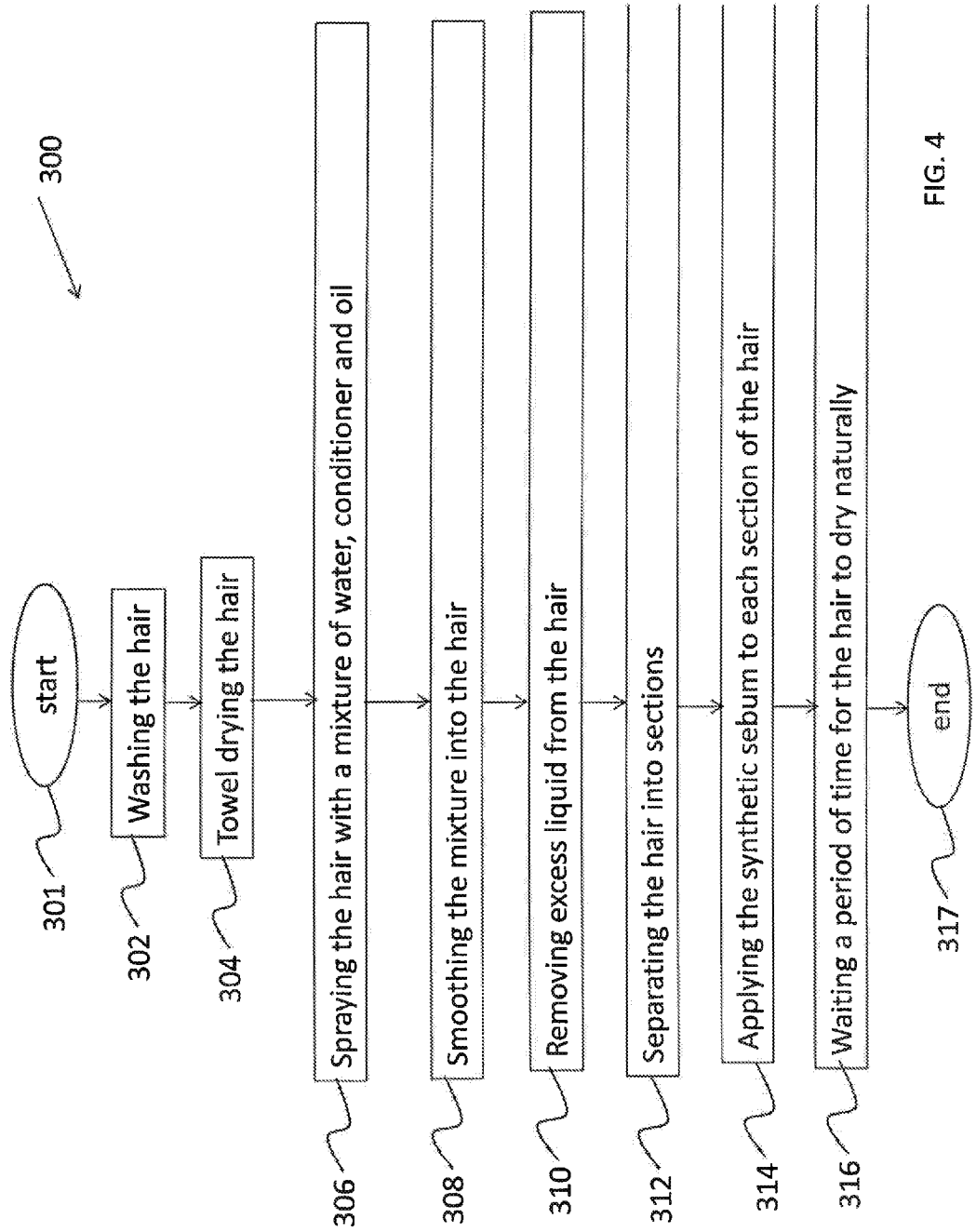
FIG. 4 illustrates a flow chart depicting a method for using the synthetic sebum for transforming hair from a first hair type to a second hair type.

FIG. 4 illustrates a flowchart depicting a method 300 for using the synthetic sebum for transforming hair from a first hair type to a second hair type. As illustrated in FIG. 4, the method 300 begins at 301 with washing 302 the hair and towel drying 304 the hair. In an exemplary embodiment, the washing 302 step involves washing the hair with shampoo, rinsing the hair with water, followed by adding conditioner to the hair and rinsing the hair, thr example. In an exemplary embodiment, the towel drying 304 step may involve using a lint free towel to remove excess water from the hair, for example. The method 300 further includes spraying 306 the hair with a mixture of water, conditioner and oil and smoothing 308 the mixture into the hair. In an exemplary embodiment, the mixture may include 12 parts water and/or 0.5-1 part conditioner and/or 0.05-0.1 part carrier oil, for example. In an exemplary embodiment, the smoothing 308 step may be performed by combing, brushing, or running fingers through the hair, for example. The method 300 further includes removing 310 excess liquid from the hair and separating 312 the hair into sections. In an exemplary embodiment, the removing 310 step may involve removing excess water from the hair with a lint free towel, for example. The method 300 further includes applying 314 the synthetic sebum formed according to the embodiments of the present invention to each section of the hair using an application technique and waiting 316 a period of time for the hair to dry naturally, before ending at 317.

The applying 314 step above may use one of several application techniques to apply the synthetic sebum to each section of the hair. For example, the application technique may be a fist application technique that involves the following steps: wrapping thumbs and fingers of a firsthand around roots of the section of hair such that hair is directed through a middle of a fist; moving the fist down from the roots to the tips of the hair section; and switching from the first hand to a second hand and repeating the wrapping and moving steps. In another example, the application technique may be a palm application technique that involves the following steps: placing a first hand with an open palm and fingers at roots of the section of hair; placing a second hand with an open palm and fingers on an opposite side of the section of hair from the first hand; and moving the first and second hand together from the roots of the section of hair to tips of the section of hair. In another example, the application technique may be a finger application technique that involves the following steps: placing the section of hair between a bended pointer finger and a thumb; and moving the finger and the thumb from the root of the section of hair to the tips of the section of hair. In another example, the application technique may be a comb or brush application technique that involves the following steps: running a comb through the section of hair from the root to the tip; and/or running a wide paddle brush with ball bristles along a rubber surface through the section of hair from the root to the tip. The application technique may be chosen, based on the hair type of the individual. For example, the fist application technique, palm application technique and finger application technique may be used for rougher hair texture. In another example, the comb/brush application technique may be used for finer hair texture. In an exemplary embodiment, washing the hair with shampoo and rinsing the hair will remove the synthetic sebum. Indeed, the body heat from the hand (i.e., fingers and palm) during the fist application technique and the palm application technique assists in blending out the synthetic sebum and in the hair pattern change. Additionally, during the applying 314 step, water may be sprayed on the hair if the synthetic sebum gets sticky or if the hair becomes too dry.

The embodiments of synthetic sebum discussed above in the present invention are not limited to the use of transformation of a first hair type to a second hair type. For example, the embodiments of the synthetic sebum discussed above may be used to form other hair styles including, but not limited to, braids, dreads, twist, or ponytails, for example. Additionally, the embodiments of the synthetic sebum may be used to slick hair back, to shape or hold hair making it pliable and flexible and/or to provide hold so as to form a range of other hair styles, for example. Furthermore, in addition to the above-discussed phases of ingredients used to form synthetic sebum, other optional ingredients such as hair gel, hair pomade, other hair dressing agents and/or other ingredients to slick hair back or form other hair styles may be used. The embodiments of the synthetic sebum discussed above in the present invention can also be used in conjunction with a flat iron and other heat styling tool or a non-heat styling tool, to straighten or make curls in the hair or change the texture or shape of curls, for example.

While the preferred embodiments of the present invention have been shown and described herein, it will be obvious that such embodiments are provided, by way of example only. Numerous variations, changes and substitutions will occur to those of skill in the art without departing from the invention herein. Accordingly, it is intended that the invention be limited only by the spirit and scope of the appended claims.

That which is claimed is:

1. A method for forming a synthetic sebum for hair, said method comprising:
    mixing water with a thickening agent at a temperature to form a first mixture; (A)
    mixing water with a sequestering agent, a first preservative and a second preservative at the temperature to form a second mixture; (B)
    mixing the first mixture and the second mixture to form a third mixture; (B)
    mixing a thickening agent with the third mixture to form a fourth mixture; (C)
    mixing an antifoam agent with the fourth mixture to form a fifth mixture; (C); and at least one of:
    mixing at least one wax with the fifth mixture; (F)
    mixing an emulsifying wax with the fifth mixture; (G); and
    mixing at least one oil with the fifth mixture; (H).

2. The method of claim 1, wherein the method comprises the step of mixing at least one wax with fifth mixture; (F).

3. The method of claim 1, wherein the method comprises the step of mixing an emulsifying wax with the fifth mixture; (G).

4. The method of claim 1, wherein the method comprises the steps of mixing at least one wax with the fifth mixture; (F) and the step of mixing an emulsifying wax with the fifth mixture; (G).

5. The method of claim 1, wherein the method comprises the step of mixing at least one oil with the fifth mixture; (H).

6. The method of claim 1, wherein the method comprises the steps of mixing at least one wax with the fifth mixture; (F) and the step of mixing at least one oil with the fifth mixture; (H).

7. The method of claim 1, wherein the method comprises the steps of mixing an emulsifying wax with the fifth mixture; (G) and the step of mixing at least one oil with the fifth mixture; (H).

8. The method of claim 1, wherein the method further comprises:
    heating the fifth mixture;
    mixing an emollient ester with the fifth mixture to form a sixth mixture;
    mixing a lubricant and a moisturizer with the sixth mixture to form a seventh mixture;
    mixing water with a thickening agent to form an eighth mixture; and
    mixing the seventh mixture and the eighth mixture.

9. The method of claim 1, wherein the forming of the synthetic sebum comprises:
    mixing between 400-600 parts of water and between 40-80 parts of thickening agent to form the first mixture;
    mixing between 230-450 parts of water, between 0.10-3.50 parts of sequestering agent, between 1-30 parts of the first preservative and between 0.10-3.50 parts of the second preservative to form the second mixture;
    mixing between 50-200 parts of the thickening agent with the third mixture to form the fourth mixture; and
    mixing between 0.01-1.0 parts of the antifoam agent with the fourth mixture to form the fifth mixture.

10. The method of claim 8, wherein the forming of the synthetic sebum comprises:
    mixing between 130-140 parts the of at least one wax and between 130-140 parts of the fifth mixture;
    mixing between 7-9 parts of the emulsifying wax and between 130-140 parts of the fifth mixture;
    mixing between 40-50 parts of the at least one oil and between 130-140 parts of the fifth mixture;
    mixing between 18-22 parts of the emollient ester with the fifth mixture to form the sixth mixture;
    mixing between 2-3 parts of the lubricant and between 14-18 parts of the moisturizer with the sixth mixture to form the seventh mixture; and
    mixing between 4-6 parts of water and between 4-6 parts of thickening agent to form the eighth mixture.

11. The method of claim 1, wherein the forming of the synthetic sebum comprises:
    corn starch as the thickening agent to form the first mixture;
    tetrasodium EDTA as the sequestering agent, sodium tetraborate decahydrate as the first preservative and sodium metabisulfite as the second preservative to form the second mixture;
    cyclocarboxypropyloleic acid potassium salt 40% solution as the thickening agent to form the fourth mixture;
    dimethicone as the antifoam agent to form the fifth mixture;
    at least one of beeswax, soy wax, jojoba ester wax and emulsifying wax as the at least one wax; and
    at least one of carrier oil, essential oil, fractionated oil, coconut oil or castor oil as the at least one oil.

12. The method of claim 1, further comprising:
    mixing at least one of a coloring additive and a fragrance additive to the fifth mixture; and
    waiting a period of time for the synthetic sebum to stand.

13. The method of claim 1, wherein the temperature is selected within a range of 60-70° C.

* * * * *